United States Patent [19]

Chou

[11] Patent Number: 4,537,959
[45] Date of Patent: Aug. 27, 1985

[54] CRYSTALLINE CEPHALOSPORIN ANTIBIOTIC SALT

[75] Inventor: Ta-Sen Chou, Indianapolis, Ind.

[73] Assignee: Eli Lilly and Company, Indianapolis, Ind.

[21] Appl. No.: 593,441

[22] Filed: Mar. 26, 1984

[51] Int. Cl.³ .................. C07D 501/38; A61K 31/545
[52] U.S. Cl. .................................................... 544/025
[58] Field of Search ....................... 544/25, 21, 22, 26; 424/246

[56] References Cited

U.S. PATENT DOCUMENTS 4,258,041  3/1981  O'Callaghan et al. .............. 424/246
4,329,453  5/1982  Brodie et al. ......................... 544/25
4,467,086  8/1984  Miller .................................. 424/246

FOREIGN PATENT DOCUMENTS 2064513  6/1981  United Kingdom .

OTHER PUBLICATIONS

Wilson, Edward M., "A Tale of Two Cephalosporins", *Chemistry & Industry*, No. 6, pp. 189–228, Mar. 19, 1984.

*Primary Examiner*—Nicholas S. Rizzo
*Attorney, Agent, or Firm*—William B. Scanlon; Arthur R. Whale

[57] ABSTRACT

Ceftazidime bishydrobromide crystalline monohydrates are provided and are useful for preparing crystalline ceftazidime pentahydrate.

1 Claim, 2 Drawing Figures

CRYSTALLINE CEPHALOSPORIN ANTIBIOTIC SALT

BACKGROUND OF THE INVENTION

This invention relates to crystalline salt forms of the cephalosporin antibiotic ceftazidime. In particular, it relates to the crystalline dihydrobromide salt of ceftazidime and to crystalline dihydrobromide monohydrates.

The antibiotic ceftazidime is disclosed in U.S. Pat. No. 4,258,041, Mar. 24, 1981, and has the chemical name (6R,7R)-7-[(Z)-2-(2-aminothiazol-4-yl)-2-(2-carboxyprop-2-oxyimino)acetamido]-3-(1-pyridiniummethyl)-3-cephem-4-carboxylate. Ceftazidime is a potent broad spectrum semi-synthetic antibiotic which can be formulated as the crystalline pentahydrate. Ceftazidime pentahydrate has been prepared with ceftazidime bishydrochloride salt as discussed in U.S. Pat. No. 4,329,453, May 11, 1982.

A crystallline ceftazidime bishydrochloride salt form is disclosed in U.K. Pat. No. 2064513.

SUMMARY

This invention provides crystalline ceftazidime bishydrobromide salt and monohydrate forms of ceftazidime bishydrobromide salt each having a discreet crystal form. The crystal forms of the bishydrobromide salt are obtained directly from the reaction mixture formed during the formic acid-HBr deblocking of the tritylamino and t-butyl ester protected ceftazidime. The crystalline forms are stable and are useful in the prepration of the known crystalline ceftazidime pentahydrate.

DETAILED DESCRIPTION

Figure 1:
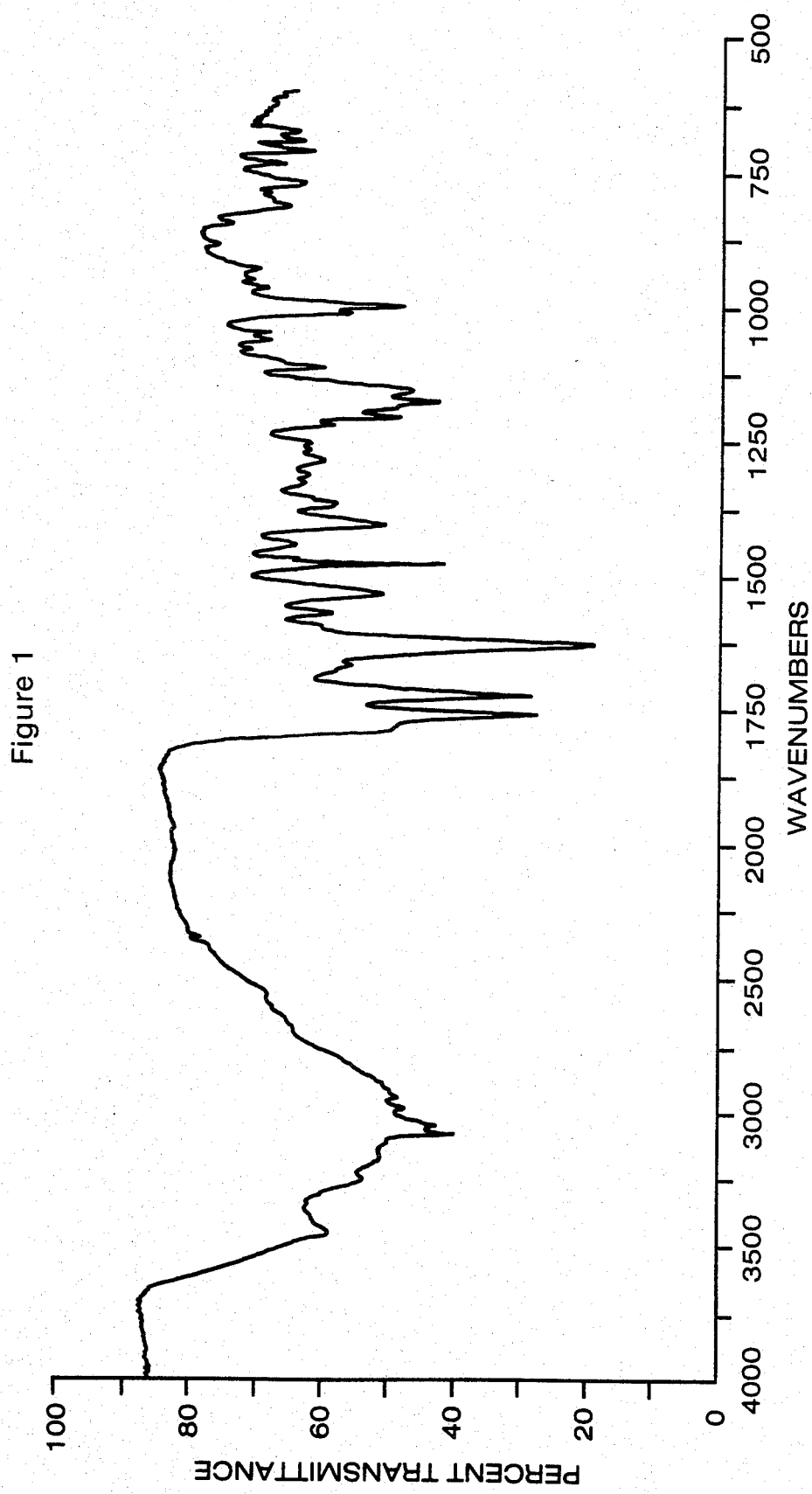
FIG. 1 is the infrared absorption spectrum of ceftazidime bishydrobromide α-monohydrate (KBr pellet).
Figure 2:
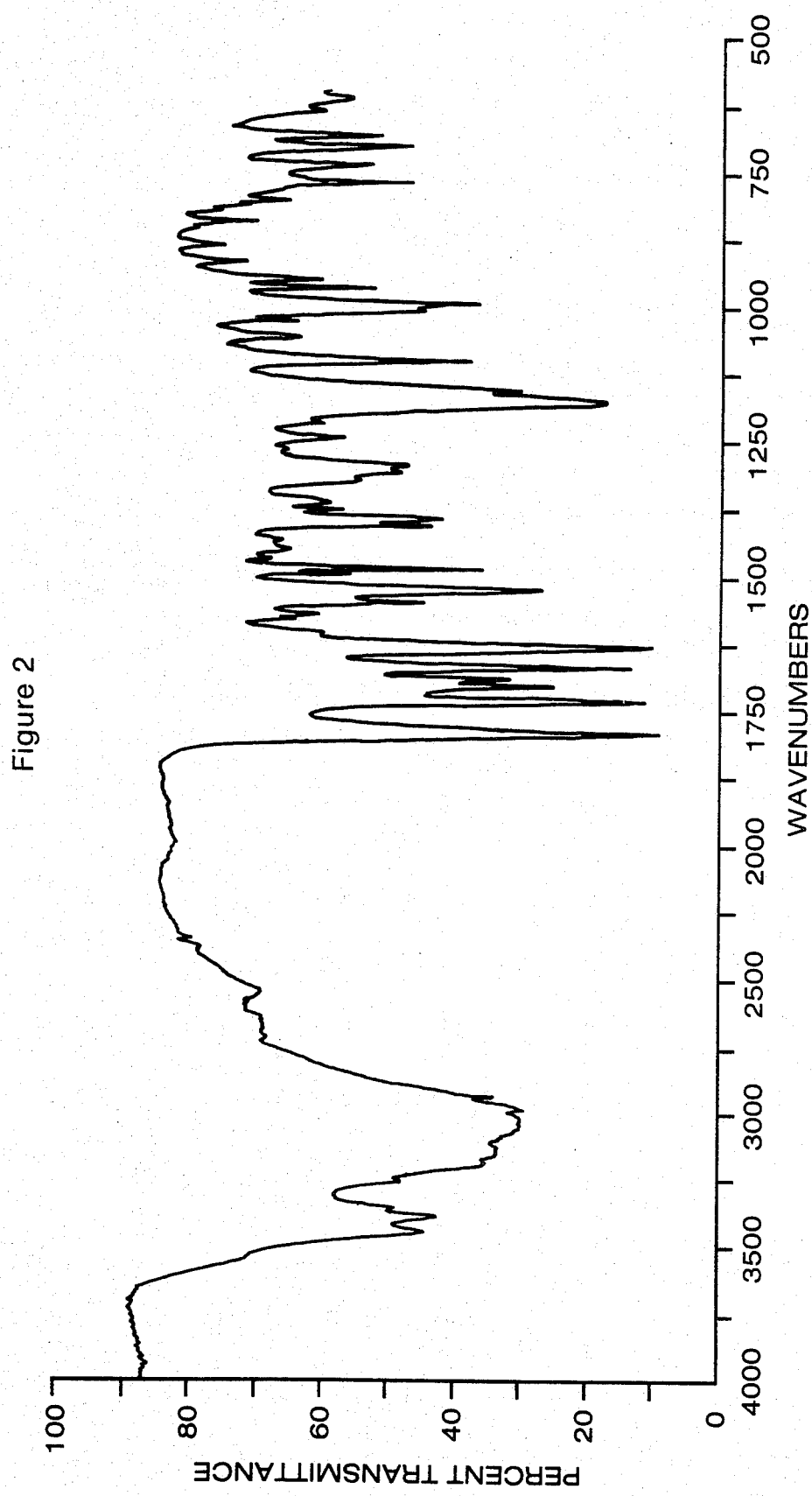
FIG. 2 is the infrared absorption spectrum of ceftazidime bishydrobromide β-monohydrate (KBr pellet).

This invention provides crystalline monohydrate forms of ceftazidime bishydrobromide designated herein as the α-monohydrate and the β-monohydrate. The α-form is usually obtained; however, the distinct β-form has been obtained. These crystalline monohydrates are characterized by their X-ray diffraction patterns and infrared spectra.

The following diffraction patterns of the two monohydrate forms were obtained using a copper target X-ray tube with a nickel filter and a 114.6 mm DeBye-Scherrer camera. The "d" refers to interplanar spacings and "I/I" to the relative intensities.

| d | I/I$_1$ | d | I/I$_1$ |
|---|---|---|---|
| α-Monohydrate | | | |
| 14.85 | .17 | 2.79 | .08 |
| 10.65 | .50 | 2.74 | .17 |
| 9.94 | .08 | 2.70 | .04 |
| 8.08 | .29 | 2.58 | .08 |
| 7.66 | .29 | | |
| | | 2.54 | .13 |
| 6.71 | .25b | 2.45 | .13 |
| 5.74 | .38 | 2.24 | .17 |
| 5.37 | .04 | 2.14 | .08 |
| 5.16 | .04 | 2.09 | .08 |
| 4.77 | .25 | | |
| 4.37 | .83 | | |
| 4.22 | 1.00 | | |
| 4.04 | .04 | | |
| 3.89 | 1.00 | | |
| 3.78 | .17 | | |
| 3.56 | .17 | | |
| 3.35 | .21 | | |
| 3.29 | .25 | | |
| 3.11 | .25 | | |
| 2.93 | .29 | | |
| 2.88 | .25 | | |
| β-Monohydrate | | | |
| 15.24 | .12 | 2.26 | .07b |
| 10.53 | .24 | 2.17 | .15 |
| 9.07 | .27 | 2.09 | .02 |
| 7.63 | .17 | | |
| 6.66 | .29 | 2.05 | .02 |
| | | 1.991 | .02 |
| 5.70 | .15 | 1.939 | .07 |
| 5.38 | .05 | | |
| 5.02 | .15b | | |
| 4.67 | .15 | | |
| 4.54 | .05 | | |
| 4.26 | .41 | | |
| 4.12 | .76 | | |
| 4.01 | .15 | | |
| 3.83 | .07 | | |
| 3.73 | 1.00 | | |
| 3.52 | .41 | | |
| 3.34 | .34b | | |
| 2.97 | .12 | | |
| 2.87 | .17b | | |
| 2.77 | .07 | | |
| 2.70 | .07 | | |
| 2.66 | .02 | | |
| 2.55 | .20 | | |
| 2.51 | .10 | | |
| 2.44 | .15 | | |
| 2.38 | .10 | | |
| 2.34 | .07 | | |

The α and β crystalline monohydrates possess the same nuclear magnetic resonance spectra and each form analyzes correctly for the percent elemental composition for ceftazidime bishydrobromide monohydrate having the empirical formula of $C_{22}H_{22}N_6O_7S_2.2HBr.H_2O$. However, the infrared absorption spectrum and the X-ray diffraction patterns of the monohydrates differ from one another. The significant absorption maxima in the spectrum of the monohydrates as shown in the drawings are listed below in Table I. The spectra were obtained on a Nicolet model 10 MX spectrophotometer.

TABLE I
Ceftazidime bishydrobromide monohydrate
Infrared Absorption Spectrum
(KBr pellet) cm$^{-1}$

| α-monohydrate | β-monohydrate |
|---|---|
| 1176.7 | 1176.7 |
| 1480.5 | 1525.8 |
| 1630.0 | 1631.9 |
| 1725.5 | 1669.5 |
| 1760.2 | 1705.2 |
| 2982.2 | 1733.2 |
| 3034.2 | 1793.9 |
| 3045.8 | 2989.9 |
| 3056.4 | 3034.2 |
| 3077.6 | 3040.0 |

The monohydrate crystalline forms of this invention can be obtained from the reaction mixture arising from the deblocking reaction wherein the ceftazidine intermediate, (6R,7R)-7-[(Z)-2-(2-tritylamino-1,3-thiazol-4-yl)-(2-t-butyloxycarbonylprop-2-oxyimino)acetamido]-3-(1-pyridiniummethyl)-3-cephem-4-carboxylate, is deprotected. The intermediate is reacted with formic acid (98%) and 48% hydrobromic acid to remove both the t-butyl carboxy-protecting group and the trityl group. The deblocked ceftazidime thus forms in solution the bishydrobromide salt. The following reaction scheme illustrates the deblocking reaction:

as the water miscible organic solvent to induce crystallization.

The α-monohydrate form of the bishydrobromide salt may be isolated from the unfiltered deblocking reaction mixture. In this instance the deblocking reaction mixture containing the insoluble triphenylcarbinol

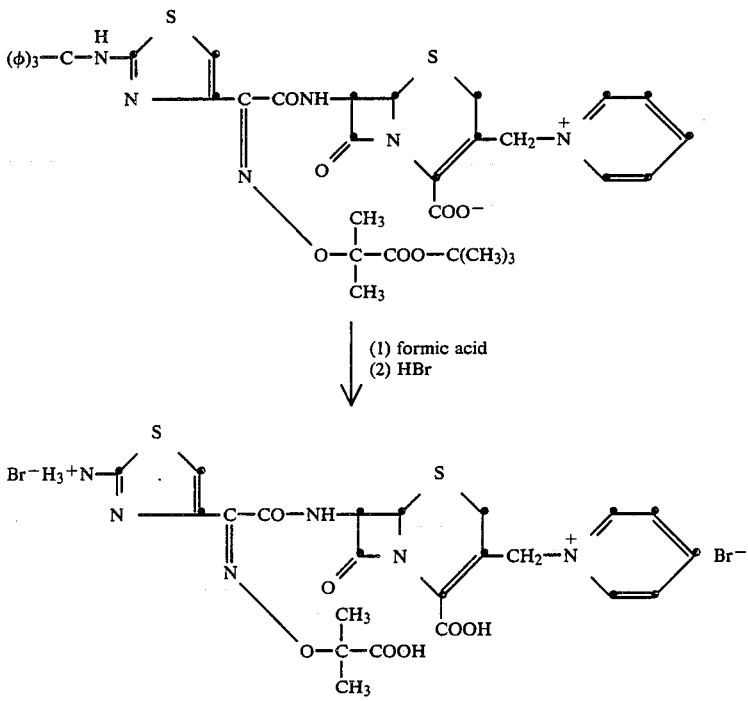

The crystalline monohydrates of the salt are isolated from the reaction mixture as follows. The deblocking reaction mixture is filtered to remove the insoluble triphenylcarbinol and the filtrate is diluted with a water miscible organic solvent to induce crystallization. The α-monohydrate is obtained crystalline with dilution by acetone, methylethyl ketone, cyclohexanone, and isopropanol. The dilution of the filtered reaction mixture with the water miscible organic solvent is generally carried out at room temerature and, following dilution, the crystallization mixture may be cooled to a temperature between about 10° C. to 20° C. to assist crystallization. In general, the filtered reaction mixture is diluted to near the cloud point or to the cloud point and the solution is chilled with stirring or allowed to stir at room temperature until crystallization occurs. With some reaction mixtures the salt may precipitate as a gum or heavy oil. The gum or oil may be induced to crystallize by redissolving the gum or oil by addition to the mixture of formic acid followed by additional diluting solvent. Alternatively, the gum or oil are separated from the mother liquor, redissolved in aqueous formic acid, and the solution diluted with the appropriate water miscible organic solvent. The crystalline ceftazidime bishydrobromide monohydrate is separated from the mother liquor by filtration and is washed with the same water miscible organic solvent used to induce crystallization. The crystalline salt is then dried at room temperature under vacuum.

The β-crystalline form has been obtained by the above procedures in which n-propyl alcohol was used is diluted with methylethyl ketone to first solubilize the carbinol. Further dilution with methylethyl ketone or acetone then induces crystallization of the dihydrobromide salt as before.

The crystalline salt monohydrates of the invention also may be prepared with ceftazidime pentahydrate or with amorphous hydrated ceftazidime. In this preparation the pentahydrate or amorphous hydrate is converted to the bishydrobromide salt with excess 48% hydrobromic acid and the acid solution is diluted with the appropriate water miscible organic solvent to induce crystallization as described hereinabove.

Preferred water miscible organic solvents for use in inducing crystallization of the α-monohydrate are methylethyl ketone and cyclohexanone. These solvents afford the largest crystals having well defined structures.

The crystalline hydrates of this invention thus far have remained stable under ordinary storage conditions for several months.

The crystalline bishydrobromide monohydrates are useful in the preparation of crystalline ceftazidime pentahydrate. The bishydrobromide monohydrate is dissolved in water or an aqueous solvent system containing a water miscible solvent. The pH of the solution is adjusted with base to about 3.5 to about 4.0 and the pentahydrate form of ceftazidime crystallizes from the solution.

The crystalline salts of this invention may also be used as active forms of ceftazidime for administration by the parenteral routes, e.g., intramuscular injection. They can be formulated with acceptable carriers, e.g., water-for-injection, 0.9% saline, or 5% glucose for injection.

The following examples further describe the preparation of the crystalline monohydrates of the invention.

EXAMPLE 1

Ceftazidime dihydrobromide β-monohydrate (6R,7R)-7-[(Z)-2-(2-tritylaminothiazol-4-yl)-2-(2-t-butyloxycarbonylprop-2-oxyimino)acetamido]-3-(1-pyridiniummethyl)-3-cephem-4-carboxylate, 18.5 g (0.02M) was added to 40 ml of 98% formic acid (53 eq.) and the mixture was maintained below a temperature of 25° C. by ice cooling during addition. The cooling bath was removed and the mixture was stirred for 2 hours at room temperature. After recooling to about 10° C. to about 15° C. 11.4 ml of 48% hydrobromic acid were added dropwise to the solution. After acid addition was complete the solution was stirred for 2 hours at room temperature. The mixture was filtered to remove the triphenylcarbinol and one-half of the filtrate (35 ml) was placed in a 250 ml flask and 52 ml of n-propyl alcohol were slowly added. When crystallization of the salt failed to occur the solution was evaporated to an oily residue. The residue was dissolved in 20 ml of n-propyl alcohol, seeded, and stirred for 30 minutes before crystallization started. The crystallization mixture was stirred overnight and the thick crystalline slurry which had formed was filtered. The crystalline salt was washed with 10 ml of n-propyl alcohol and dried in vacuo at room temperature. There were obtained 5.50 g of the dihydrobromide β-monohydrate salt as a white crystalline solid.

Elemental analysis of crystalline salt β-monohydrate after drying at 40° C.: Calculated for $C_{22}H_{22}N_6O_7S_2.2HBr.H_2O$: Theory: C, 36.38; H, 3.61; N, 11.57; O, 17.62; S, 8.83; Br, 22.00. Found: C, 36.12; H, 3.48; N, 11.33; O, 17.87; S, 8.61; Br, 22.07.

Mass Spectral Analysis: M/e 547.

m.p.: starts to decompose at 175° C.

EXAMPLE 2

Ceftazidime bishydrobromide α-monohydrate

The amino-protected and carboxy-protected ceftazidime intermediate, (6R,7R)-7-[(Z)-2-(2-tritylamino-1,3-thiazol-4-yl)-2-(2-t-butyloxycarbonylprop-2-oxyimino)acetamido]-3-(1-pyridiniummethyl)-3-cephem-4-carboxylate 18.5 g, was treated with formic acid and 48% hydrobromic acid using the same conditions and quantities as described in Example 1. The reaction mixture was not filtered to remove triphenylcarbinol as was done in Example 1, but, instead, 150 ml of methylethyl ketone (MEK) were slowly added to the mixture. A clear solution was obtained. An additional 304 ml of MEK were added over 45 minutes. The product salt formed an insoluble oily gum and an additional 100 ml of MEK were added. After stirring the reaction mixture for 30 minutes at room temperature the mixture was warmed to a temperature of about 70° C. to about 75° C. The gum began to crystallize in the warm mixture which was then cooled to a temperature of 5°–10° C. After the mixture was stirred in the cold for 30 minutes the crystals were filtered, washed with 50 ml of cold MEK, and dried in vacuo at room temperature to afford 4.48 g of fraction A of the bishydrobromide α-monohydrate. A second fraction B of 6.82 g of the crystalline salt (darker in color) were obtained.

Fraction A elemental analysis after drying the sample at 40° C. calculated for $C_{22}H_{22}N_6O_7S_2.2HBr.H_2O$: Theory: C, 36.38; H, 3.61; N, 11.57; O, 17.62; S, 8.83; Br, 22.00 Found: C, 36.12; H, 3.36; N, 11.33; O, 17.76; S, 8.72; Br, 22.26.

EXAMPLE 3

Ceftazidime bishydrobromide α-monohydrate

The trityl amino-protected and t-butyl ester protected ceftazidime used in the preceeding examples, 18.0 g, was added to 40 ml of 98% formic acid. The temperature of the mixture was maintained below about 25° C. with an ice bath. The reaction mixture was stirred for 30 minutes and 11.8 ml of 48% hydrobromic acid were added dropwise with stirring to the mixture. The acid mixture was stirred for 3.5 hours and was filtered to remove the insoluble triphenylmethanol. The filtrate was divided into two equal volumes and one-half (31 ml) was added dropwise with stirring to 185 ml of methylethyl ketone. As the addition of the filtrate proceeded crystalline monohydrate began to precipitate. An additional 50 ml of methylethyl ketone were added and the mixture was stirred at room temperature for 1.5 hours. The crystalline α-monohydrate was filtered, washed with 50 ml of the ketone, and dried at room temperature in vacuo. The white crystalline α-monohydrate weighed 5.50 g.

The other half of the filtered deblocking reaction mixture (31 ml) was added dropwise with stirring to 185 ml of cyclohexanone at room temperature. Some white precipitate formed and when about one-half of the filtrate had been added some gum formation was observed. The rest of the filtrate was added and the mixture was stirred for about 2 hours with some crystal formation. The mixture was allowed to stir overnight with formation of a quantity of dense crystals. The crystals were filtered, washed with 50 ml of cyclohexanone and dried without heating in vacuo. There were obtained 4.68 g of the crystalline α-monohydrate melting at about 177° C. with decomposition.

Elemental analysis of a sample of the product after drying at 40° C. gave the following results when calculated for $C_{22}H_{22}N_6O_7S_2.2HBr.H_2O$: Theory: C, 36.38; H, 3.61; N, 11.57; O, 17.62; S, 8.83; Br, 22.00. Found: C, 36.67; H, 3.57; N, 11.47; O, 17.52; S, 8.97; Br, 21.89.

Mass Spectral Analysis: M/e 547.

m.p.: starts to decompose at 175° C.

I claim:

1. The α-monohydrate crystalline form of ceftazidime bishydrobromide having the following X-ray diffraction pattern:

| d | $I/I_1$ |
|---|---|
| 14.85 | .17 |
| 10.65 | .50 |
| 9.94 | .08 |
| 8.08 | .29 |
| 7.66 | .29 |
| 6.71 | .25b |
| 5.74 | .38 |
| 5.37 | .04 |
| 5.16 | .04 |
| 4.77 | .25 |
| 4.37 | .83 |
| 4.22 | 1.00 |
| 4.04 | .04 |
| 3.89 | 1.00 |
| 3.78 | .17 |
| 3.56 | .17 |
| 3.35 | .21 |
| 3.29 | .25 |

-continued

| d | I/I$_1$ |
|---|---|
| 3.11 | .25 |
| 2.93 | .29 |
| 2.88 | .25 |
| 2.79 | .08 |
| 2.74 | .17 |

-continued

| d | I/I$_1$ |
|---|---|
| 2.70 | .04 |
| 2.58 | .08 |
| 2.54 | .13 |
| 2.45 | .13 |
| 2.24 | .17 |
| 2.14 | .08 |
| 2.09 | .08 |

* * * * *